(12) United States Patent
Li et al.

(10) Patent No.: US 11,312,687 B2
(45) Date of Patent: Apr. 26, 2022

(54) 7H-AZULENE [1,2,3-I,J] ISOQUINOLIN-7-ONE COMPOUND, SINGLE CRYSTAL AND USE THEREOF

(71) Applicant: Hunan University of Chinese Medicine, Hunan (CN)

(72) Inventors: Shunxiang Li, Hunan (CN); Juan Li, Hunan (CN)

(73) Assignee: HUNAN UNIVERSITY OF CHINESE MEDICINE, Hunan (CN)

( * ) Notice: Subject to any disclaimer, the term of this patent is extended or adjusted under 35 U.S.C. 154(b) by 0 days.

(21) Appl. No.: 16/097,776

(22) PCT Filed: Mar. 22, 2018

(86) PCT No.: PCT/CN2018/080074
§ 371 (c)(1),
(2) Date: Mar. 1, 2019

(87) PCT Pub. No.: WO2018/171684
PCT Pub. Date: Sep. 27, 2018

(65) Prior Publication Data
US 2019/0194138 A1 Jun. 27, 2019

(30) Foreign Application Priority Data
Mar. 22, 2017 (CN) .......................... 201710173690.4

(51) Int. Cl.
| C07D 221/18 | (2006.01) |
| B01D 15/08 | (2006.01) |
| B01D 11/02 | (2006.01) |
| A61K 31/00 | (2006.01) |
| B01D 11/04 | (2006.01) |

(52) U.S. Cl.
CPC ............ C07D 221/18 (2013.01); A61K 31/00 (2013.01); B01D 11/0288 (2013.01); B01D 11/0492 (2013.01); B01D 15/08 (2013.01); C07B 2200/13 (2013.01)

(58) Field of Classification Search
CPC .................................................. C07D 221/18
See application file for complete search history.

(56) References Cited

FOREIGN PATENT DOCUMENTS

CN 1973877 A * 6/2007

OTHER PUBLICATIONS

Han, H. "Targeted Prodrug Design to Optimize Drug Delivery." AAPS Pharmsci. (2000), vol. 2 (1) article 6, pp. 1-11. (Year: 2000).*
Ettmayer, P., et al. "Lessons Learned from Marketed and Investigational Prodrugs." J. Med. Chem. (2004) 47(10), pp. 2393-2404. (Year: 2004).*
Testa, B. "Prodrug research: futile or fertile?" Biochem. Pharm. (2004) 68, pp. 2097-2106. (Year: 2004).*
Berge, Stephen M., et al. "Pharmaceutical Salts." Journal of Pharmaceutical Sciences. (Jan. 1977), vol. 66, No. 1, pp. 1-19. (Year: 1977).*
Li, J., et al. "A Novel Tropoloisoquinoline Alkaloid, Neotatarine, from Acorus calamus L." Chem. Biodiversity (2017), vol. 14, e1700201, pp. 1-6 of 6. (Year: 2017).*
Machine English-language translation of CN1973877A, WIPO Translation. (Year: 2007).*
Liu, Yun-Xi, et al. "Effects and molecular mechanisms of the antidiabetic fraction of Acorus calamus L. on GLP-1 expression and secretion in vivo and in vitro." Journal of Ethnopharmacology. (2015), vol. 166, pp. 168-175. (Year: 2015).*

* cited by examiner

*Primary Examiner* — John S Kenyon

(57) ABSTRACT

A 7H-azulene [1,2,3-i,j] isoquinolin-7-one compound, a single crystal and a use thereof are provided. The compound has a structure as shown in a formula (I). The present invention obtains a crude extract of *Acorus calamus* L., then extracts with different polar solvents in sequence and separates column chromatography to obtain a novel alkaloid compound, which is expected to be developed into a novel class of drug exerting neuroprotective effects, so as to prevent and treat senile dementia, stroke and epilepsy diseases.

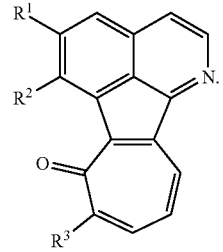

formula (I)

5 Claims, 9 Drawing Sheets

7H-AZULENE [1,2,3-I,J] ISOQUINOLIN-7-ONE COMPOUND, SINGLE CRYSTAL AND USE THEREOF

BACKGROUND OF THE PRESET INVENTION

Field of Invention

The present invention relates to a novel class of alkaloids, and more particularly to the compounds having a mother nucleus structural of 7H-azulene [1,2,3-i,j] isoquinolin-7-one, and medicament, preparation method, single crystal and use in disease treatment of the compounds.

Description of Related Arts

Alzheimer's disease (AD), also known as senile dementia, is a neurological degenerative disease that develops insidiously. The primary risk factor for Alzheimer's disease is age, and the prevalence of the disease increases with age (about 10% of individuals over 65 years old and about 50% of individuals over 85 years old). After the age of 65, the incidence of disease will be doubled every 5 years, and about 1275 new cases are annually diagnosed from every 100,000 people over 65 years old. There is a real and urgent need for drugs that can delay the onset of Alzheimer's disease and provide effective treatments.

Epilepsy is a serious disease common for the central nervous system, whose prevalence is the third highest in neurological diseases. There are approximately 50 million patients worldwide. The clinical manifestations of patients with epilepsy are mainly unpredictable seizures. Its pathological basis is the excessive excitement of neurons. Conventional listed anti-epileptic drugs are mainly used to control convulsions: reduce the frequency of seizures and shorten the onset time. However, there was no significant improvement in the overall pathological process of epilepsy. Moreover, approximately 30% of patients are resistant to these conventional treatments. Therefore, there is an urgent need to develop new drugs for the treatment of epilepsy.

Cerebral stroke, also known as stroke and cerebrovascular accident, is an acute cerebrovascular disease caused by a sudden rupture of blood vessels in the brain or blood that cannot flow into the brain due to vascular occlusion. It is also urgent to develop drugs for the treatment and prevention of stroke.

*Acorus calamus* L is a member of the genus *Acorus*, the Araceae family. It is contained in the "Shennong's Herbal Classic" and is listed as the top grade, which is a commonly used traditional Chinese medicine. During the Dragon Boat Festival, folks often hang *Acorus calamus* L., scent folium artemisiae argyi, wear sachet pouch, bath with *Acorus calamus* L., etc. so as to avoid evil, disease and plague. "Chinese Materia Medica" records that *Acorus calamus* L. has the effect of removing phlegm, strengthening spleen, killing insects and relieving itching, so as to treating coma due to blocking of the respiratory system, stroke, epilepsy, convulsions and forgetfulness, tinnitus and deafness, dyspepsia and abdominal pain, diarrhea, rheumatism, eczema, and hemorrhoids. Modern pharmaceutical research shows that it comprises sesquiterpenoids, phenylpropanoids, alkaloids, fatty acids and other chemical components, having biological activities such as anti-acetylcholinesterase, anti-amnesia, anti-epilepsy, antibacterial, insecticidal, antihypertensive, hypolipidemic, anti-tumor, hypoglycemic and anti-inflammatory.

Chinese patent application CN200610155051.7 discloses an extract of an effective part of *Acorus calamus* L. and a use thereof, which are prepared by extracting an aqueous solution which is 50-60% of a root volume, filtering and combining filtrate, recovering the solvent to obtain a dry paste; suspending the dry paste in distilled water; extracting by water, n-butanol, ethyl acetate and petroleum ether in sequence, and respectively recovering the solvent for obtaining the water extracting portion, the n-butanol extract, the ethyl acetate extracting portion and the petroleum ether portion. The effective fraction is preferably the ethyl acetate extracting portion. The extract of the effective fraction contains isoproton diol, WLJ-9, β-carotene, β-asarone, β-sitosterol and cetyl acid as main active ingredients. The effective extract is used in combination with an excipient which is permitted by the formulation for the preparation of a medicament for the prevention and treatment of diabetes. There are no reports about the alkaloid active ingredients of 7H-azulene [1,2,3-i,j] isoquinolin-7-one structure, and its application in the prevention and treatment of senile dementia, cerebral stroke and epilepsy.

SUMMARY OF THE PRESENT INVENTION

The present invention systematically studies chemical constituents of *Acorus calamus* L., and obtains a crude extract; then extracts with different polar solvents in sequence and separates column chromatography to obtain a novel alkaloid compound, which is expected to be developed into a novel class of drug exerting neuroprotective effects, so as to prevent and treat senile dementia, stroke and epilepsy diseases.

Accordingly, the present invention provides the compounds having the structure of 7H-azulene isoquinolin-7-one, which are the compounds as shown in the formula (I); or stereoisomer, oxynitride, pharmaceutically acceptable salt or prodrug of the compounds as shown in the formula (I):

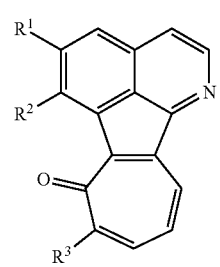

formula (I)

wherein, each of $R^1$, $R^2$ and $R^3$ is independently hydrogen, hydrazine, F, Cl, Br, I, hydroxy, amino, nitro, cyano, $C_{1-6}$ alkyl, hydroxy $C_{1-6}$ alkyl, amino $C_{1-6}$ alkyl, $C_{1-6}$ haloalkyl, $C_{1-6}$ haloalkoxy, $C_{1-6}$ alkoxy $C_{1-6}$ alkyl, $C_{2-6}$ alkenyl, $C_{2-6}$ alkynyl, $C_{1-6}$ alkylamino, or $C_{1-6}$ alkoxy; or carbon atoms attached between $R^1$ and $R^2$ together form an oxygen-containing $C_{2-7}$ heterocycle.

Preferably, the present invention provides a compound as shown in the formula (I); or a stereoisomer, an oxynitride, a pharmaceutically acceptable salt or a prodrug of the compound as shown in the formula (I), wherein, each of $R^1$, $R^2$ and $R^3$ is independently hydrogen, hydrazine, F, Cl, Br, I, hydroxy, amino, nitro, cyano, $C_{1-4}$ alkyl, hydroxy $C_{1-4}$ alkyl, amino $C_{1-4}$ alkyl, $C_{1-4}$ haloalkyl, $C_{1-4}$ haloalkoxy, $C_{1-4}$ alkoxy $C_{1-4}$ alkyl, $C_{2-6}$ alkenyl, $C_{2-6}$ alkynyl, $C_{1-4}$ alkylamino, or $C_{1-4}$ alkoxy; or carbon atoms attached between $R^1$ and $R^2$ together form oxygen-containing $C_{2-5}$ heterocycle.

Preferably, the present invention provides a compound as shown in the formula (I); or a stereoisomer, an oxynitride, a pharmaceutically acceptable salt or a prodrug of the compound as shown in the formula (I), wherein, each of $R^1$, $R^2$ and $R^3$ is independently hydrogen, hydrazine, F, Cl, Br, I, hydroxy, amino, nitro, cyano, methyl, ethyl, n-propyl, isopropyl, n-butyl, hydroxymethyl, 1-hydroxyethyl, methoxy, ethoxy, n-propoxy, isopropoxy or n-butoxy group, or carbon atoms attached between $R^1$ and $R^2$ together form oxygen-containing cyclopropane, cyclobutane, cyclopentane or cyclohexane.

Preferably, the present invention provides a compound with one of following structures; or a stereoisomer, an oxynitride, a pharmaceutically acceptable salt or a prodrug of the compound with one of the following structures:

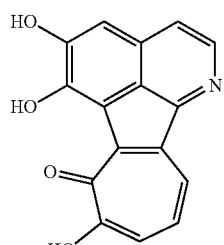
(1)

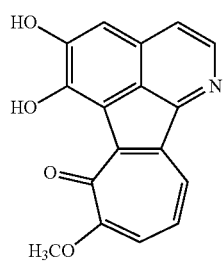
(2)

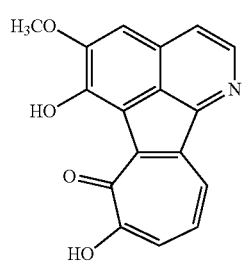
(3)

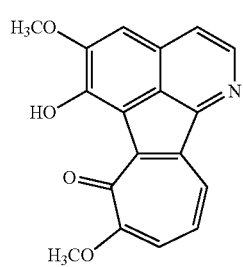
(4)

-continued

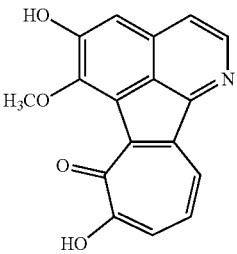
(5)

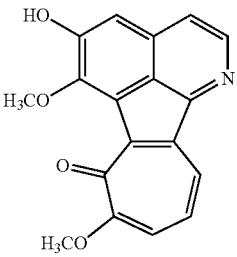
(6)

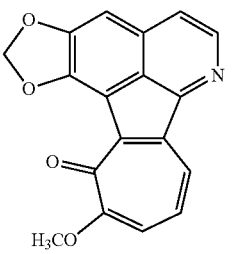
(7)

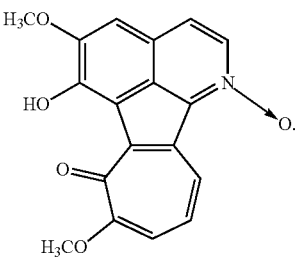
(8)

Furthermore, the present invention provides a single crystal of the compound as shown in the formula (II), wherein the single crystal has following parameters of single crystal structure:

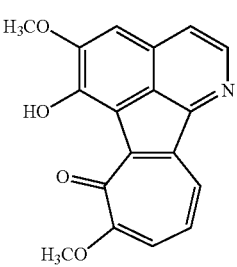
formula (II)

| | |
|---|---|
| crystal system | monoclinic system |
| space group | P121/c1 |
| cell parameters | a = 7.5352(8) Å, α = 90°, |

| | |
|---|---|
| | b = 11.7589(10) Å, β = 95.301(6)° |
| | c = 15.6709(14) Å, γ = 90°, |
| volume | 1382.6(2) Å³ |
| number of molecules per unit cell Z: | 4. |

Furthermore, the present invention provides a pharmaceutical composition comprising the compound as mentioned above, and a pharmaceutically acceptable carrier, an excipient, a diluent, an adjuvant, a vehicle or a combination thereof.

Furthermore, the present invention provides a method for preparing a medicament for preventing, treating, curing or ameliorating diseases caused by damaged nerve cells, comprising using the compound as mentioned above, or the pharmaceutical composition as mentioned above.

Preferably, the diseases are caused by damaged nerve cells comprise, but are not limited to, Alzheimer's disease, cerebral stroke, or epilepsy.

Furthermore, the present invention provides a method for preparing the single crystal, comprising steps of: dissolving a crude product of the formula (II) in a solvent and standing, sealing when crystals are precipitated, keeping stand to obtain the single crystal.

Preferably, the solvent is methanol, ethanol, chloroform or a mixed solution of chloroform-methanol.

Preferably, dissolving the crude product in the solvent and standing means that the solution dissolved in the solvent is allowed to stand at a room temperature to slowly evaporate the solvent.

Preferably, keeping stand means that the solution having crystal precipitation is sealed and allowed to stand for 7 to 10 days.

Preferably, the single crystal is a deep red crystal.

Furthermore, the present invention provides a salt of the compound of the formula (II), wherein the salt may be hydrochloride, hydrobromide, sulfate, nitrate, phosphate, methanesulfonate or benzene sulfonate, p-toluenesulfonate, malate, lactate, succinate or butenedioate.

Furthermore, the present invention provides a method for preparing a compound as shown in a formula (II), comprising steps of: washing rhizomes of *Acorus calamus* L. for removing impurities, drying in shade, pulverizing into coarse powder, extracting with an alcohol solvent, and concentrating an extract under a reduced pressure until the extract is viscous, so as to obtain an alcohol extract;

suspending the alcohol extract in water, extracting with different polar solvents in sequence, concentrating a solvent extract under a reduced pressure; and separating residue by column chromatography to obtain a crude product of 6-hydroxy-5,8-dimethoxy-7H-azulene [1,2,3-i,j] isoquinolin-7-one as shown in the formula (II).

Preferably, the column chromatography uses silica gel, MCI gel or Sephadex LH-20 gel as a packing material for separating.

The alcohol solvent is a $C_{1-4}$ alcohol solvent, preferably ethanol or methanol.

Preferably, water is distilled water or purified water.

The different polar solvents are cyclohexane, petroleum ether, chloroform, dichloromethane, ethyl acetate, n-butanol or a combination thereof.

Furthermore, an amount of the alcohol reagent is 5-10 times weight of the medicinal material, and a concentration of the alcohol reagent is 80-95%.

The present invention systematically studies chemical constituents of *Acorus calamus* L., and obtains a crude extract with alcohol reagent; then extracts with different polar solvents in sequence, concentrate different extract solvents, then systematically separates and identifies structure of the compound. A novel compound is separated from the *Acorus calamus* L.: 6-hydroxy-5,8-dimethoxy-7H-azulene [1,2,3-i,j] isoquinolin-7-one (shown in the formula (II), which has significant protective effect on damaged nerve cells according to detection of protective effects on damaged nerve cells. The compound is expected to be developed into a novel class of drug exerting neuroprotective effects, so as to prevent and treat senile dementia, stroke and epilepsy diseases.

In addition, the preparation method provided by the present invention is simple, the process route is feasible, the utilization rate of the medicinal material is high, and the solvent generated in the production process can be reused. The present invention is eco-friendly and is suitable for industrial production.

Definitions and General Terms

Unless otherwise indicated, all technical and scientific terms used in the present invention have the same meaning as commonly understood by one of ordinary skill in the art. All patents and publications related to the present invention are hereby incorporated by reference in their entirety. Although any methods and materials similar or equivalent to those described herein can be used in the practice or testing of the present invention, the preferred methods, devices, and materials are described in the present invention.

The following definitions used herein should be applied unless otherwise stated. For the purposes of the present invention, chemical elements are consistent with the CAS version of the Periodic Table of the Elements, and the Handbook of Chemistry and Physics, 75th Edition, 1994.

The term "patient" as used in the present invention refers to a person (including adults and children) or other animals. Preferably, "patient" refers to a person.

The term "comprising" is an open-ended expression that includes the subject matter of the present invention, but does not exclude other aspects.

"Stereoisomer" refers to a compound that has the same chemical structure but differs in the way the atoms or groups are spatially aligned. Stereoisomers include enantiomers, diastereomers, conformational isomers (rotomers), geometric isomers (cis/trans) isomers, atropisomers, etc.

Many organic compounds exist in optically active forms, i.e., they have the ability to rotate the plane of plane polarized light. In describing optically active compounds, the prefixes D and L or R and S are used to indicate the absolute configuration of the molecule with respect to one or more of its chiral centers. The prefixes d and l or (+) and (−) are symbols for specifying the rotation of plane polarized to light caused by a compound, wherein (−) or l indicates that the compound is left-handed, and (+) or d indicates that the compound is right-handed. A particular stereoisomer is an enantiomer, and a mixture of such isomers is referred to as an enantiomers mixture. A 50:50 mixture of enantiomers is referred to as a racemic mixture or a racemate, which can occur when there is no stereoselectivity or stereospecificity in a chemical reaction or process.

"Pharmaceutically acceptable" means such compounds, materials, compositions and/or dosage forms, within the scope of sound medical judgment, which are suitable for use in contact with the patient's tissue without undue toxicity, irritation, allergies or other problems and complications commensurate with a reasonable benefit/risk ratio; and are effective for the intended use.

As described herein, the compounds of the present invention may be optionally substituted with one or more substituents, such as the compounds of the above formula, or specific examples and subclasses described in the embodiments, and a class of compounds of the present invention.

In addition, it should be noted that the descriptions of the "individually" and "respectively" and "independently" are interchangeable, unless otherwise explicitly indicated in the present invention. Such descriptions should be understood in a broad sense, which can mean that the specific options expressed between the same symbols in different groups do not affect with each other, and can also represent specific options expressed in the same group and between the same symbols. There is no influence between each other.

In various portions of the specification, substituents of the compounds disclosed herein are disclosed in terms of the type or range of groups. In particular, the present invention includes each individual sub-combination of each member of the group and range of such groups. For example, the term "$C_{1-6}$ alkyl" specifically refers to independently disclosed methyl, ethyl, $C_3$ alkyl, $C_4$ alkyl, $C_5$ alkyl, and $C_6$ alkyl.

The term "alkyl" or "alkyl group" as used herein, which denotes a saturated straight or branched chain monovalent hydrocarbon group containing from 1 to 6 carbon atoms, wherein the alkyl group can be optionally substituted with one or more substituents described herein. Unless otherwise specified, an alkyl group contains from 1 to 6 carbon atoms; in another embodiment, the alkyl group contains from 1 to 4 carbon atoms; and in yet another embodiment, the alkyl group contains 1-3 carbon atoms. Examples of alkyl groups include, but are not limited to, methyl, ethyl, n-propyl, isopropyl, n-butyl, isobutyl, sec-butyl, tert-butyl, n-pentyl, 2-pentyl Base, 3-pentyl, 2-methyl-2-butyl, n-hexyl, n-heptyl, n-octyl, and the like.

The term "alkenyl" denotes a straight or branched chain monovalent hydrocarbon radical containing from 2 to 6 carbon atoms, wherein at least one site is unsaturated, i.e., having a carbon-carbon sp2 double bond; wherein the alkenyl group can be optionally substituted with one or more substituents described herein, including "cis" and "tans" positioning, or "E" and "Z" positioning. In one embodiment, the alkenyl group contains 2 to 6 carbon atoms; in another embodiment, the alkenyl group contains 2 to 4 carbon atoms. Examples of alkenyl groups include, but are not limited to, vinyl, allyl, and the like.

The term "alkynyl" denotes a straight or branched chain monovalent hydrocarbon radical containing from 2 to 6 carbon atoms, wherein at least one site is unsaturated, i.e., having a carbon-carbon sp triple bond, wherein the alkynyl group can be optionally substituted with one or more substituents described herein. In one embodiment, the alkynyl group contains 2 to 6 carbon atoms; in another embodiment, the alkynyl group contains 2 to 4 carbon atoms. Examples of alkynyl groups include, but are not limited to, ethynyl, propargyl, 1-propynyl, and the like.

The term "alkoxy" denotes an alkyl group attached to the remainder of the molecule through an oxygen atom, wherein the alkyl group has the meaning as described herein. Unless otherwise specified, the alkoxy group contains from 1 to 6 carbon atoms. In one embodiment, the alkoxy group contains from 1 to 6 carbon atoms; in another embodiment, the alkoxy group contains from 1 to 4 carbon atoms; in yet another embodiment, the alkoxy group contains 1-3 carbon atoms. The alkoxy group can be optionally substituted with one or more substituents described herein. Examples of alkoxy groups include, but are not limited to, methoxy, ethoxy, propoxy, and the like.

The term "alkoxyalkyl" denotes an alkyl group substituted by one or more alkoxy groups, examples of which include, but are not limited to, methoxymethyl, ethoxymethyl and the like.

The term "haloalkyl", "haloalkenyl" or "haloalkoxy" denotes an alkyl, alkenyl or alkoxy group substituted by one or more halogen atoms, examples of which include, but are not limited to, trifluoromethyl, 2,2,3,3-tetrafluoropropyl, trifluoromethoxy, and the like.

The terms "heterocyclyl" and "heterocycle" are used interchangeably herein to refer to a saturated or partially unsaturated non-aromatic monocyclic, bicyclic or tricyclic ring containing 3 to 12 ring atoms. According to the present invention, at least one ring atom of the heterocycle is an oxygen atom, and may further optionally contain nitrogen or sulfur atoms, and the —$CH_2$— group may be optionally substituted by —C(=O)—. The sulfur atom of the ring can be optionally oxidized to an S-oxide. The nitrogen atom of the ring can be optionally oxidized to an N-oxygen compound. Examples of heterocyclic groups include, but are not limited to, oxiranyl, oxetanyl, tetrahydrofuranyl, dihydrofuranyl, 1,3-dioxocyclopentyl, tetrahydropyranyl, dihydropyridyl cyclo, 2H-pyranyl, 4H-pyranyl, tetrahydrothiopyranyl, piperidinyl, morpholinyl, thiomorpholinyl, piperazinyl, dioxoalkyl, dithiaalkyl, thia O-alkyl, homopiperazinyl, homopiperidinyl, and the like.

The term "halogen" means fluorine (F), chlorine (Cl), bromine (Br) or iodine (I).

The term "alkylamino" or "alkylamino" includes "N-alkylamino" and "N,N-dialkylamino", wherein the amino groups are independently substituted with one or two alkyl groups. In some of the embodiments, the alkylamino group is a lower alkylamino group having one or two $C_{1-6}$ alkyl groups attached to the nitrogen atom. In other embodiments, the alkylamino group is a lower alkylamino group of $C_{1-3}$. Suitable alkylamino groups may be monoalkylamino or dialkylamino, examples of which include, but are not limited to, N-methylamino, N-ethylamino, N,N-dimethylamino, N, N-diethylamino and the like.

The term "aminoalkyl" includes $C_{1-6}$ straight or branched alkyl groups substituted with one or more amino groups. In some embodiments, the aminoalkyl group is a $C_{1-6}$ "lower aminoalkyl group" substituted with one or more amino groups. In other embodiments, the aminoalkyl group is a $C_{1-4}$ "lower aminoalkyl group" substituted with one or more amino groups. Such examples include, but are not limited to, aminomethyl, aminoethyl, aminopropyl, aminobutyl and aminohexyl.

The term "hydroxyalkyl" embraces a $C_{1-6}$ straight or branched alkyl group substituted with one or more hydroxy groups. In some embodiments, the hydroxyalkyl group is a $C_{1-6}$ "lower hydroxyalkyl group" substituted with one or more hydroxy groups, and in other embodiments, the hydroxyalkyl group is a $C_{1-4}$ "lower hydroxyalkyl group" substituted with one or more hydroxy groups. Such examples include, but are not limited to, hydroxymethyl, hydroxyethyl, hydroxypropyl, hydroxybutyl and hydroxyhexyl.

The term "prodrug" as used in the present invention denotes a compound which will be converted in vivo to a compound of the formula (I) or (II). Such transformation is affected by the hydrolysis of the prodrug in the blood or by enzymatic conversion to the parent structure in blood or tissue. The prodrug-like compound of the present invention may be an ester. In the prior art, the ester may be used as a prodrug of a phenyl ester, an aliphatic ($C_{1-24}$) ester, an acyloxymethyl ester, a carbonate, carbamates and amino acid esters. For example, a compound of the present invention comprises a hydroxyl group, i.e., it can be acylated to give a compound in the form of a prodrug.

The "pharmaceutically acceptable salt" as used in the present invention means an organic salt and an inorganic salt of the compound of the present invention. Salts formed by pharmaceutically acceptable non-toxic acids include, but are not limited to, hydrochloride, hydrobromide, sulfate, nitrate, phosphate, methanesulfonate, besylate, p-toluenesulfonate, malate, lactate, succinate or butenedioate.

The X-ray single crystal detector uses low-energy X-rays to quickly detect the object without damaging the object to be inspected. The position of the X-ray single crystal diffraction peak depends mainly on the crystal structure and is relatively insensitive to experimental details, and its relative peak height depends on many factors related to sample preparation and instrument geometry. Determining the symmetry of the crystal and the range of crystal orientation can be used to observe crystal defects and study the crystal integrity.

As described herein, the pharmaceutically acceptable compositions of the present invention further comprise a pharmaceutically acceptable carrier, adjuvant, or excipient, such as any solvent, diluent, or other liquid excipients, dispersing or suspending agents, surfactants, isotonic agents, thickeners, emulsifiers, preservatives, solid binders or lubricants, etc., suitable for particular target dosage form. Except for any conventional carrier medium incompatible with the compounds of formula (I) or (II) of the present invention, for example, any undesirable biological effects produced or any detrimental interaction with other components of the pharmaceutically acceptable composition, their uses are also within the scope of the present invention.

Substances which may be used as pharmaceutically acceptable carriers include, but are not limited to, ion exchangers; aluminum; aluminum stearate; lecithin; serum proteins such as human serum albumin; buffer substances such as phosphate; glycine; sorbic acid; potassium acid; a partial glyceride mixture of saturated vegetable fatty acids; water; salt or electrolyte, such as protamine sulfate, disodium hydrogen phosphate, potassium hydrogen phosphate, sodium chloride, zinc salt; colloidal silicon; magnesium trisilicate; pyrrolidone; polyacrylate; wax; polyethylene-polyoxypropylene-blocking polymer; lanolin; sugars such as lactose, glucose and sucrose; starches such as corn starch and potato starch; cellulose and its derivatives such as carboxymethyl cellulose sodium, ethyl cellulose and cellulose acetate; gum powder; malt; gelatin; talc powder; excipients such as cocoa butter and suppository wax; oils such as peanut oil, cottonseed oil, safflower oil, sesame oil, olive oil, corn oil and soybean oil; glycol compounds such as propylene glycol and polyethylene glycol; esters such as ethyl oleate and ethyl laurate; agar; buffers such as magnesium hydroxide and aluminum hydroxide; seaweed acid pyrogen-free water; isotonic salt; Ringer's solution; ethanol; phosphate buffer solution; and other non-toxic suitable lubricants such as sodium lauryl sulfate and magnesium stearate; colorants; release agents; coating materials; sweeteners; flavoring agents; flavors; preservatives and antioxidants.

The compounds disclosed herein are typically formulated in a dosage form suitable for administration to a patient by the desired route. For example, dosage forms include those suitable for the following routes of administration: (1) oral administration, such as tablets (common tablets, chewable tablets, effervescent tablets, buccal tablets, coated tablets, etc.), capsules, pills, syrups, elixirs, suspensions, solutions, emulsions and powders; (2) parenteral administration, such as injections, sterile solutions, suspensions, and lyophilized powders; (3) transdermal administration, such as transdermal patch; (4) rectal administration, such as a suppository; (5) inhalation, such as an aerosol, a solution, and a dry powder; and (6) topical administration, such as a cream, ointment, wash agents, solutions, pastes, sprays and gels.

The compounds of the formula (I) an (II) of the present invention can be administered in the form of an oral preparation such as a tablet, a capsule (each of which includes a sustained release or timed release formulation), a pill, a powder, an elixir, an expectorant, suspensions, syrups and emulsifiers. They may also be administered in the form of intravenous, intraperitoneal, subcutaneous or intramuscular, all of which are well known to those of ordinary skill in the pharmaceutical arts. They can be administered alone, but will generally be administered with a selected pharmaceutical carrier based on the mode of administration chosen and standard pharmaceutical practice.

DETAILED DESCRIPTION OF THE PREFERRED EMBODIMENT

Figure 1:
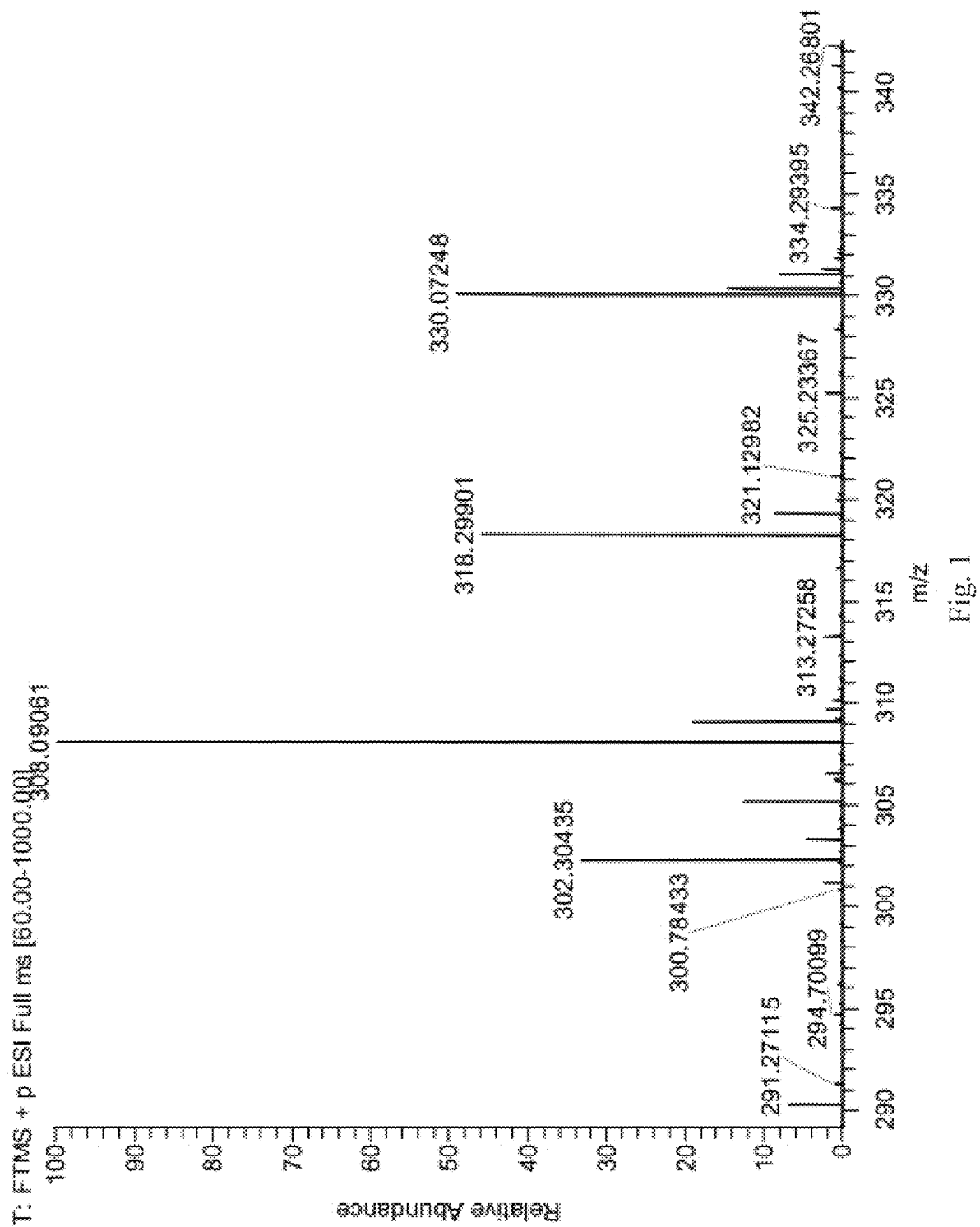
FIG. 1 HR-ESI-MS spectrum of 6-hydroxy-5,8-dimethoxy-7H-azulene [1,2,3-i,j] isoquinolin-7-one.
Figure 2:
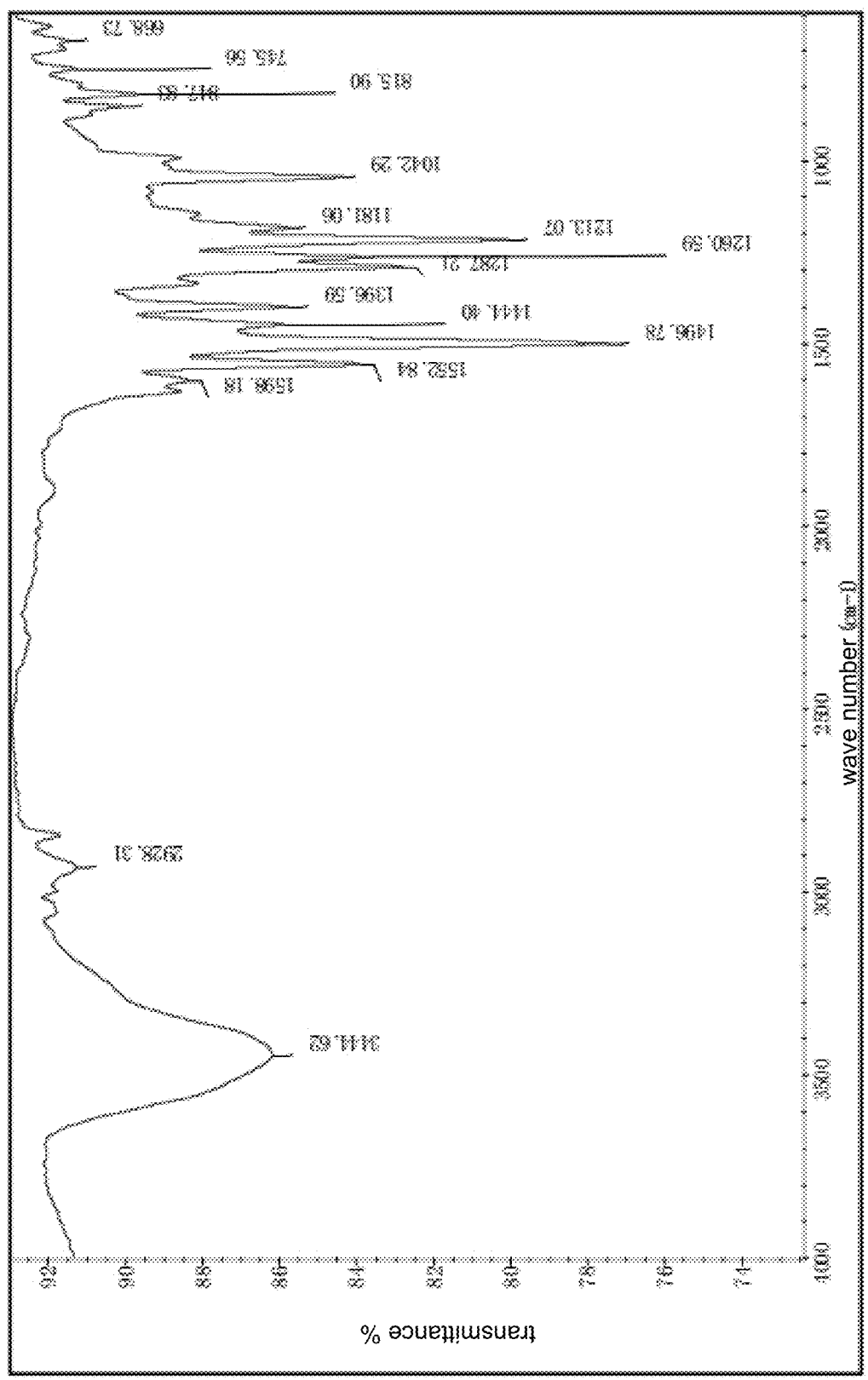
FIG. 2 IR spectrum of 6-hydroxy-5,8-dimethoxy-7H-azulene [1,2,3-i,j] isoquinolin-7-one.
Figure 3:
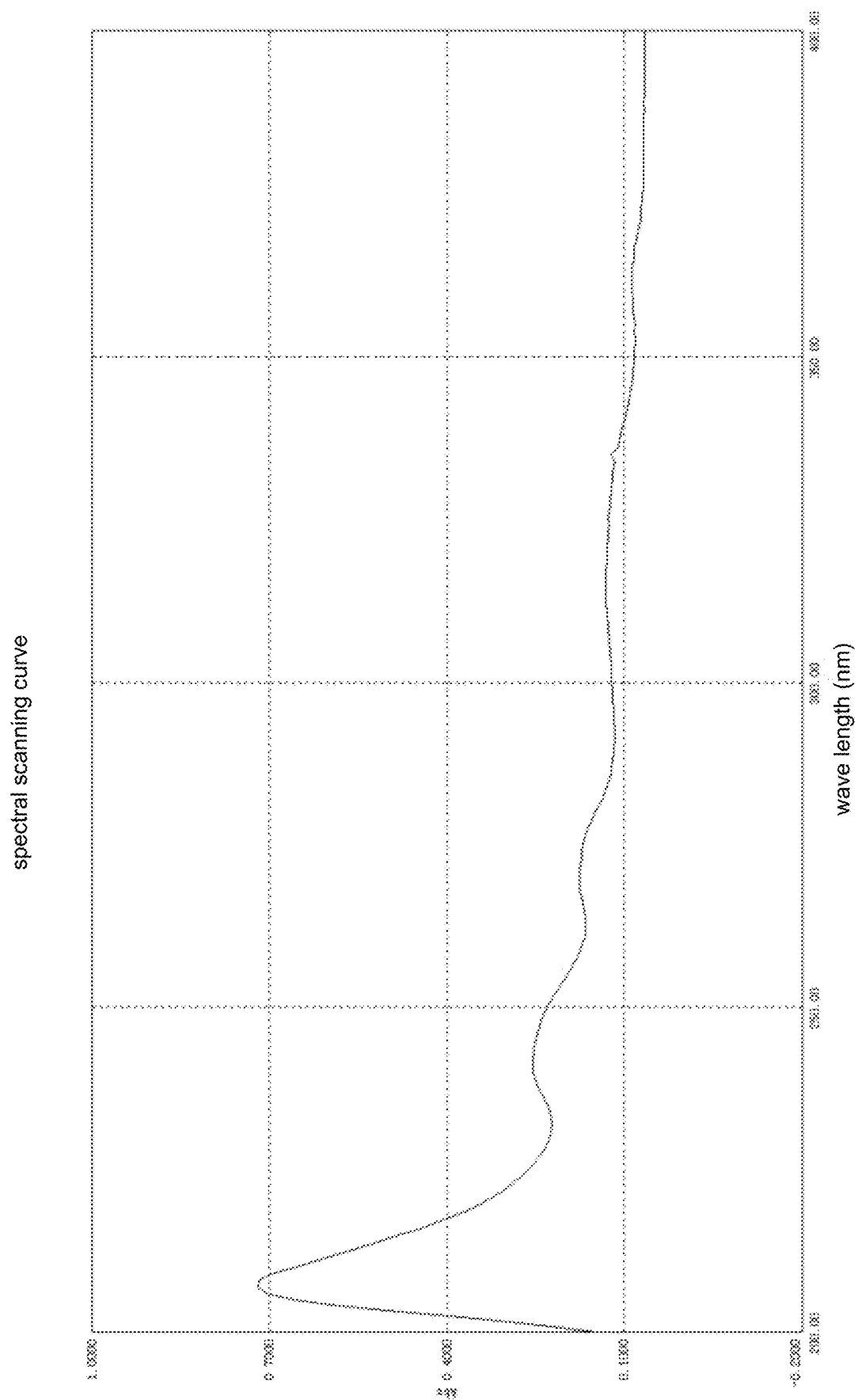
FIG. 3 UV spectrum of 6-hydroxy-5,8-dimethoxy-7H-azulene [1,2,3-i,j] isoquinolin-7-one.
Figure 4:
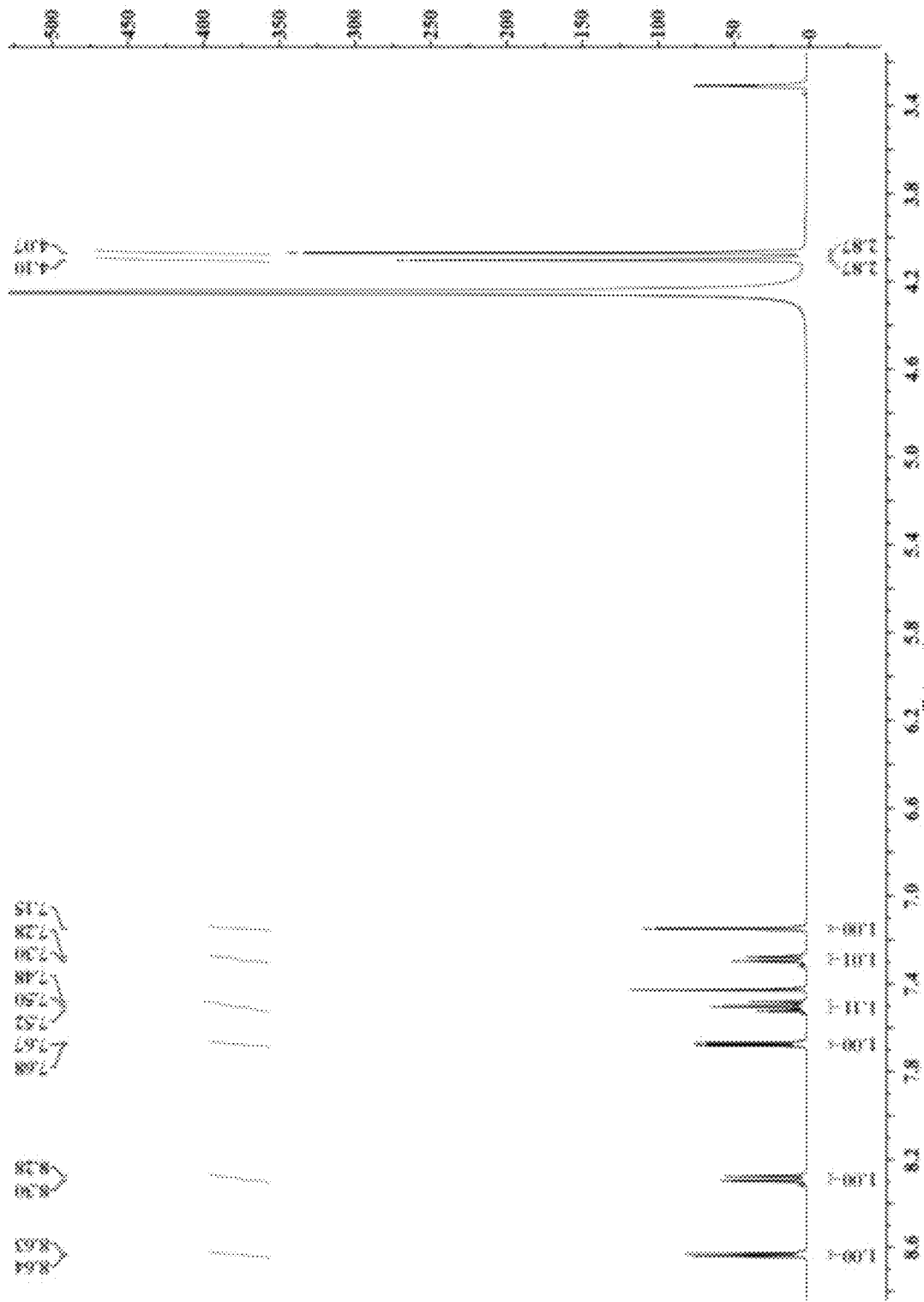
FIG. 4 $^1$H NMR spectrum of 6-hydroxy-5,8-dimethoxy-7H-azulene [1,2,3-i,j] isoquinolin-7-one.
Figure 5:
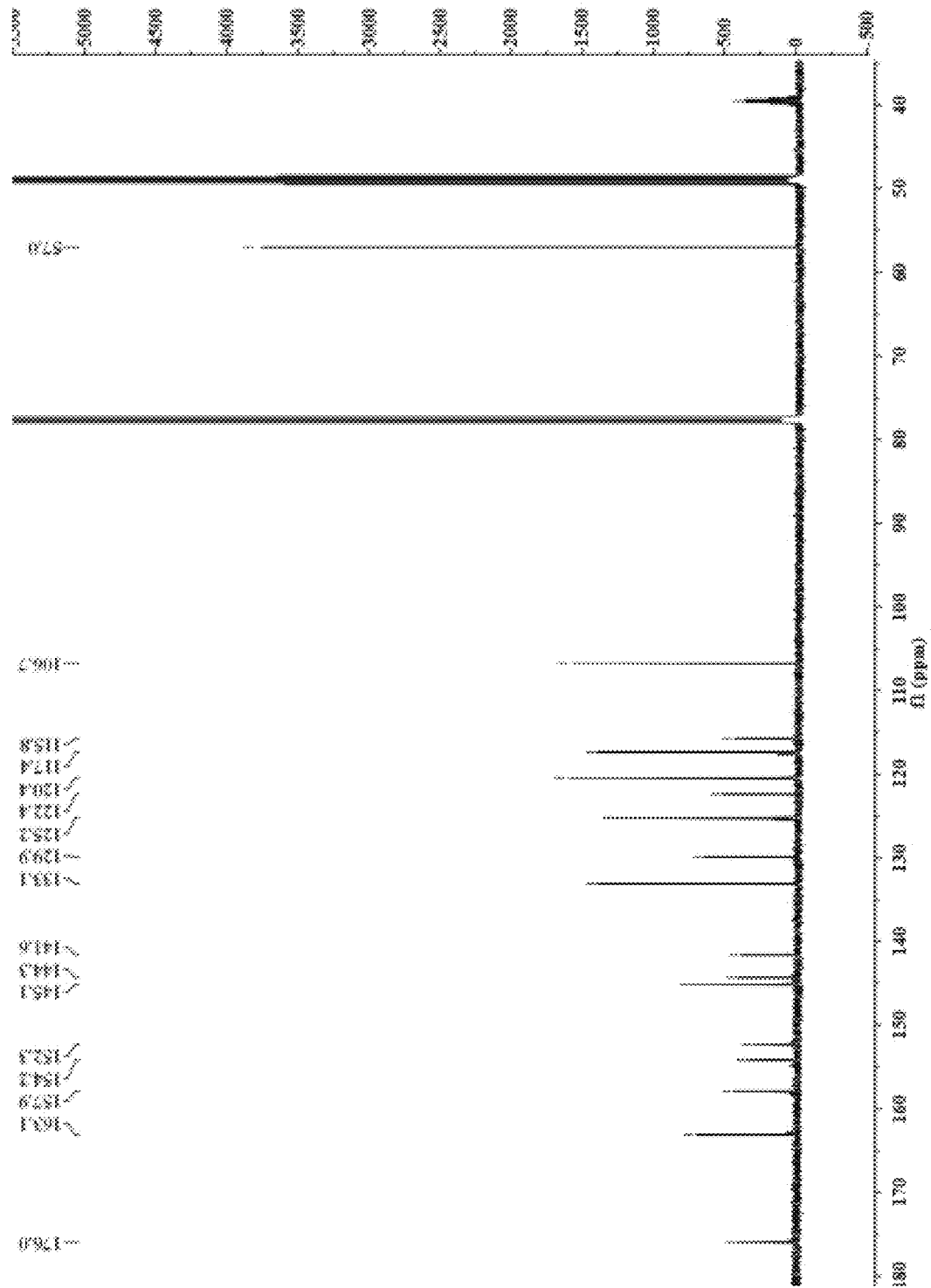
FIG. 5 $^{13}$C NMR spectrum of 6-hydroxy-5,8-dimethoxy-7H-azulene [1,2,3-i,j] isoquinolin-7-one.
Figure 6:
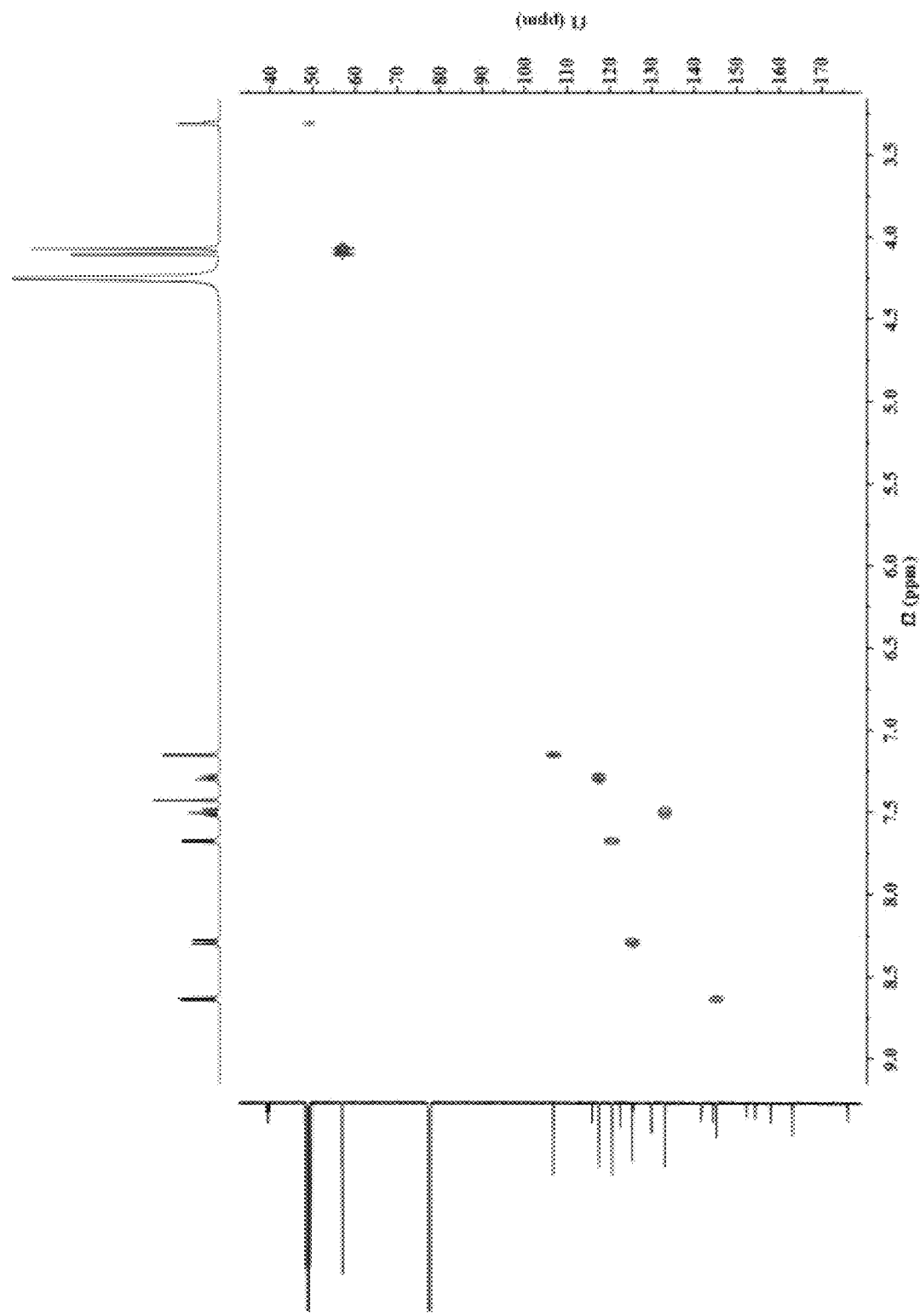
FIG. 6 HSQC spectrum of 6-hydroxy-5,8-dimethoxy-7H-azulene [1,2,3-i,j] isoquinolin-7-one.
Figure 7:
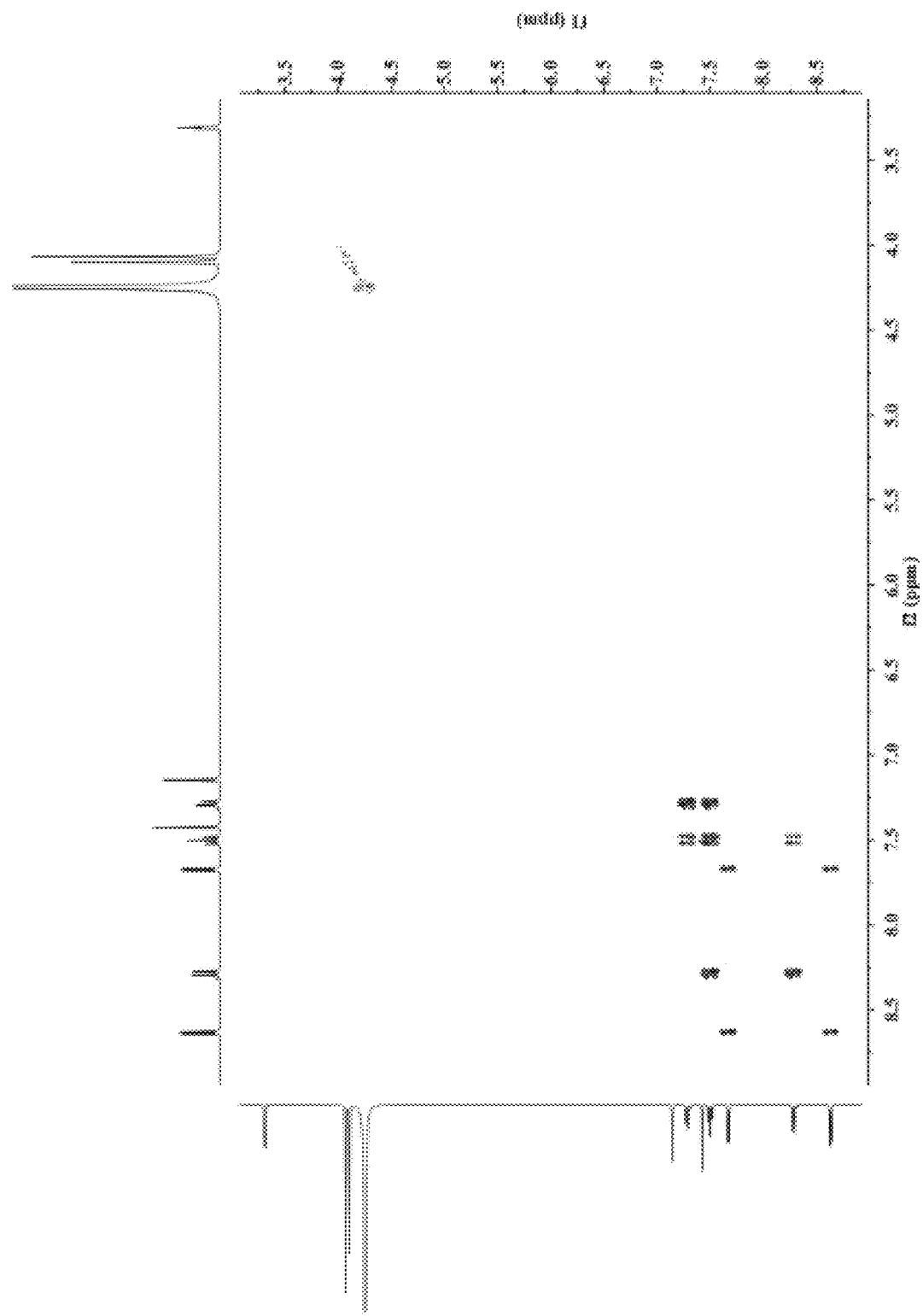
FIG. 7 $^1$H-$^1$H COSY spectrum of 6-hydroxy-5,8-dimethoxy-7H-azulene [1,2,3-i,j] isoquinolin-7-one.
Figure 8:
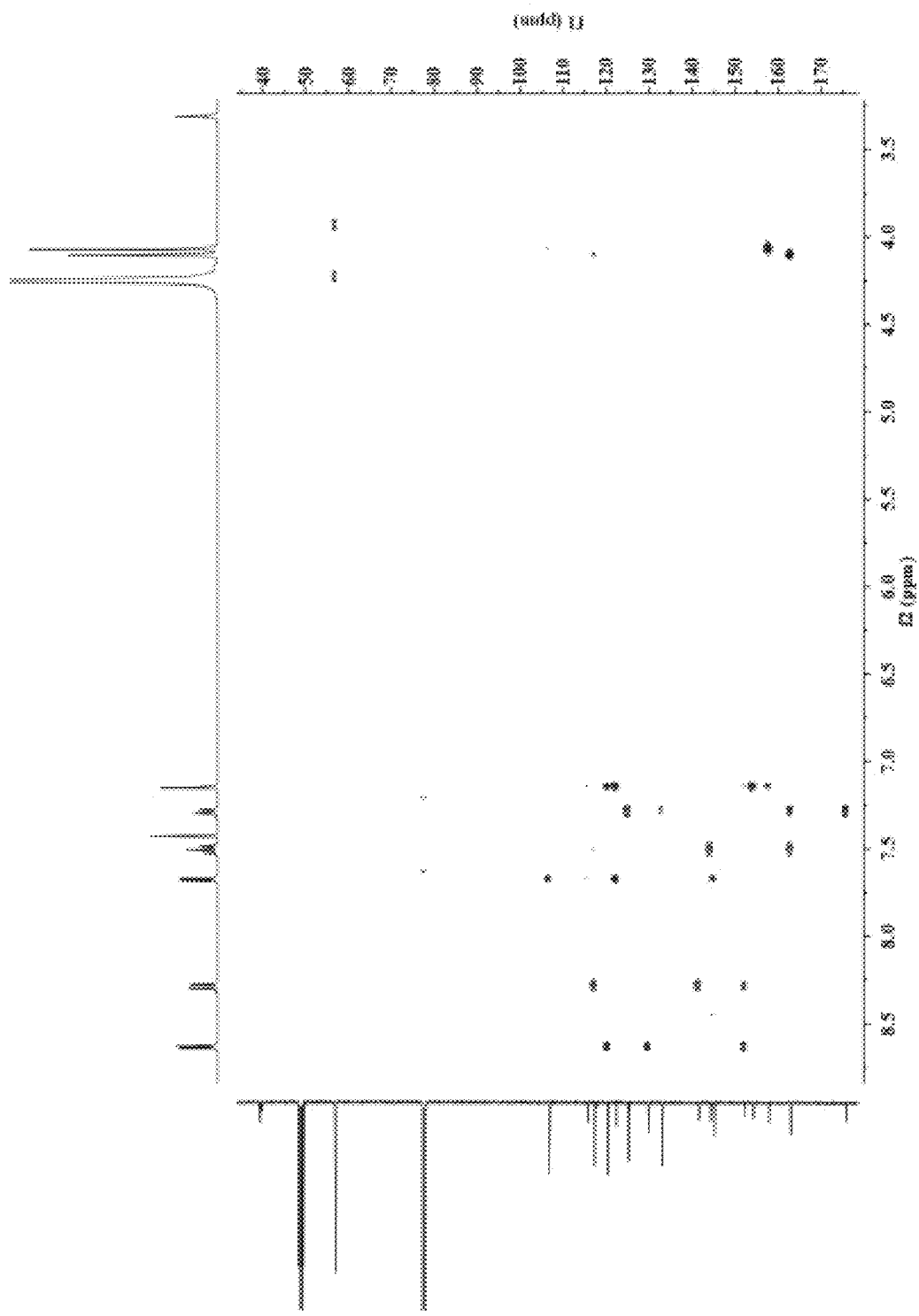
FIG. 8 HMBC spectrum of 6-hydroxy-5,8-dimethoxy-7H-azulene isoquinolin-7-one.

The present invention will be further illustrated with the following embodiments but is not limited thereby. Those skilled in the art can learn from the contents of the specification and appropriately improve the process parameters. It is to be understood that all such alternatives and modifications are Obvious to those skilled in the art and are considered to be included in the present invention. The method and the application of the present invention have been described by the preferred embodiments, and it is obvious that the method and application described herein may be modified or appropriately modified and combined without departing from the scope of the present invention.

Embodiment 1

Preparation of Crude Product of 6-hydroxy-5,8-dimethoxy-7H-azulene [1,2,3-i,j] isoquinolin-7-one Pulverizing dried rhizomes (10 kg) of *Acorus calamus* L. into coarse powder, and extracting medicinal materials with 95% ethanol four times at room temperature for 24 h each time; combining extract, and then concentrating under reduced pressure at 45° C. to obtain an ethanol extract (weighs 1.1 kg).

Adding 1 L distilled water into obtained ethanol extract for suspending, and extracting with petroleum ether (1 L×5 times) and chloroform (1 L×5 times) in sequence; concentrating under reduced pressure to obtain a petroleum ether extract (extract 1 weighs 618.6 g) and a chloroform extract (extract 2 weighs 58.9 g).

Eluting the extract 2 through silica gel column chromatography (200-300 mesh, 6.0×100 cm, 1.0 kg) with a gradient of petroleum ether-acetone (50:1→0.1), so as to obtain 6 fragments (Fr. 1-Fr. 6), eluting Fr. 4 (9.0 g) through Sephadex LH-20 column with petroleum ether-chloroform-methanol (4:5:1) (flow rate of 15 drops·min$^{-1}$). so as to obtain crude product of 6-hydroxy-5,8-dimethoxy-7H-azulene [1,2,3-i,j] isoquinolin-7-one (weighs 5 mg).

Embodiment 2

Preparation of Single Crystal of 6-hydroxy-5,8-dimethoxy-7H-azulene [1,2,3-i,j] isoquinolin-7-one Dissolving 5 mg crude product of 6-hydroxy-5,8-dimethoxy-7H-azulene [1,2,3-i,j] isoquinolin-7-one obtained in the embodiment 1 into 2-3 L ethanol, slowly volatilizing obtained solution at a room temperature, and sealing when crystals are precipitated; waiting for 7 to 10 days before filtering, adding a small amount of ethanol to wash surfaces of filter residue, and drying residue at room temperature, so as to obtain a deep red needle crystal, weighs of the single crystal, 4.25 mg, wherein a yield is 85%.

Embodiment 3

Structure Identification of 6-hydroxy-5,8-dimethoxy-7H-azulene [1,2,3-i,j] isoquinolin-7-one 6-hydroxy-5,8-dimethoxy-7H-azulene [1,2,3-i,j] isoquinolin-7-one is dark red needle crystal. mp>254° C., yellow fluorescence under TLC ultraviolet lamp (254 nm), showing brownish red by modified Dragendorff's reagent.

UV (MeOH) λ$_{max}$ (log ε) 207 nm (3.82), 242 nm (3.37), 269 nm (3.21), 314 nm (3.08), 335 nm (3.06).

IR spectrum shows the existence of hydroxyl group (3444 cm$^{-1}$) and phenyl ring (1598, 1553, 1497 and 1444 cm$^{-1}$) functional groups.

HR-ESI-MS m/z 308.09061 [M+H]$^+$ (calcd. for $C_{18}H_{14}NO_4$ 308.09228), 330.07248 [M+Na]$^+$ (calcd. for $C_{18}H_{13}NO_4Na$ 330.07423), which is determined to have a molecular formula of $C_{18}H_{13}NO_4$ and an unsaturation degree of 13.

According to NMR data, the compound has 18 carbons, including ten quaternary carbons, six tertiary carbons, and two methyl carbons. $^1$H NMR spectrum (see Table 1) shows two methoxy methyl signals δ$_H$ 4.07 (3H, s, 5-OCH$_3$) and 4.10 (3H, s, 8-OCH$_3$); a set of each coupled olefinic protons signals δ$_H$ 8.64 (1H, d, J=5.0 Hz, H-2) and 7.68 (1H, d, J=5.0 Hz, H-3), indicating there are two ortho-hydrogen protons at the 2,3 position on the isoquinoline ring; another set of each coupled olefinic proton signals δ$_H$ 7.29 (1H, d, J=10.0 Hz, H-9), 7.50 (1H, t, J=10.0 Hz, H-10) and 8.29 (1H, d, J=10.0 Hz, H-11). $^{13}$C NMR spectrum (see Table 1) shows a ketone carbonyl carbon signal δ$_C$ 176.0 (C-7), three oxygenated quaternary carbon signals δ$_C$ 157.9 (C-5), 154.2 (C-6), 163.1 (C-8), and two oxygenated methyl carbon signals δ$_C$ 57.0 (5, 8-OCH$_3$); According to the molecular formula, there is interred to be one hydroxyl group in the structure.

TABLE 1

NMR data of 6-hydroxy-5,8-dimethoxy-7H-azulene [1,2,3-i,j] isoquinolin-7-one

| No. | δ$_C$ (ppm) | δ$_H$ (ppm, J in Hz) | $^1$H-$^1$H COSY | HMBC (H→C) |
|---|---|---|---|---|
| 2 | 145.1 | 8.64 (1H, d, 5.0) | H-3 | 3, 3a, 11b |
| 3 | 120.4 | 7.68 (1H, d, 5.0) | H-2 | 2, 3b, 4 |
| 3a | 129.9 | | | |
| 3b | 122.4 | | | |
| 4 | 106.7 | 7.15 (1H, s) | | 3, 3b, 5, 6 |
| 5 | 157.9 | | | |
| 6 | 154.2 | | | |
| 6a | 115.8 | | | |
| 6b | 141.6 | | | |
| 7 | 176.0 | | | |
| 8 | 163.1 | | | |
| 9 | 117.4 | 7.29 (1H, d, 10.0) | H-10 | 7, 8, 10, 11 |
| 10 | 133.1 | 7.50 (1H, t, 10.0) | H-9, H-11 | 8, 11a |
| 11 | 125.2 | 8.29 (1H, d, 10.0) | H-10 | 6b, 9, 11b |
| 11a | 144.3 | | | |
| 11b | 152.3 | | | |
| 5-OCH$_3$ | 57.0 | 4.07 (3H, s) | | 5 |
| 8-OCH$_3$ | 57.0 | 4.10 (3H, s) | | 8 |

$^1$H NMR (500 MHz, CDCl$_3$/CD$_3$OD/DMSO-d$_6$ (1:1:0.25)) and $^{13}$C NMR (125 MHz, CDCl$_3$/CD$_3$OD/DMSO-d$_6$ (1:1:0.25)).

Cross-signal peaks of the $^1$H-$^1$H COSY spectrum indicates that the compound has two proton-bearing structural fragments, corresponding to H-9/H-10/H-11 and H-2/H-3. In HMBC spectrum, strong correlations from 5-OCH$_3$ to C-5, 8-OCH$_3$ to C-8, indicating that two methoxy groups are respectively attached at the C-5 and C-8 positions. HMBC correlations from H-9/H-10 to C-8 indicate that C-8 is connected to C-9; HMBC correlation from H-9 to C-7 indicates that C-7 is connected to C-8; HMBC correlation from H-10 to C-11a indicates that C-11a is connected to C-11; and HMBC correlations from H-11 to C-6b/C-11b indicates that C-11b and C-6b are connected to C-11a. Chemical shift of a C-6b position is towards a low field, which may be affected by π-π conjugated effect of carbony group. According to the above information, the structure is initially inferred as the formula (III). The above analysis is as shown in the formula (III).

Formula (III): structure, key $^1$H-$^1$H COSY and HMBC correlations of 6-hydroxy-5,8-dimethoxy-7H-azulene [1,2,3-i,j] isoquinolin-7-one

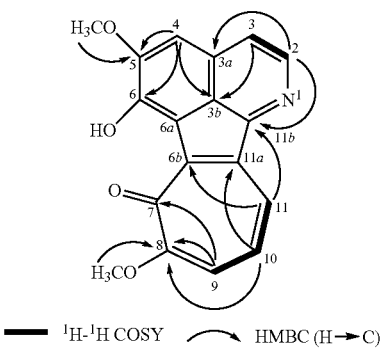

Embodiment 4

Single Crystal Structure of 6-hydroxy-5,8-dimethoxy-7H-azulene [1,2,3-i,j] isoquinolin-7-one

(1) X-Ray Single Crystal Diffraction Method for Measuring Structure

Selecting a single crystal of 0.050×0.080×0.150 mm³, and collecting diffraction data with a BRUKER SMART APEX 1000 CCD diffractometer, wherein Mo Kα ray (λ=0.071073 nm) monochromated by a graphite monochromator is used at 296(2) K for collecting the diffraction data by ω-φ scanning. Using Broker's SAINTPLUS program to restore data and use SADABS program for empirical absorption correction. Directly resolving and refining the structure with SHEXLS-97 and SHELXL-97 programs [Sheldrick, G. M. SHELXS97 and SHELXL97 University of Gottingen, Germany, 2008]. Structurally refining all non-hydrogen atoms with full matrix least squares; and anisotropically refining all non-hydrogen atoms. With theoretical hydrogenation and modification of hydrogen atom isotropic thermal parameters, crystal data and structural parameters are listed in Table 2.

TABLE 2 crystal data and structural parameters of 6-hydroxy-5,8-dimethoxy-7H-azulene [1,2,3-i,j] isoquinolin-7-one

| Item | Data |
|---|---|
| Chemical formula | $C_{18}H_{13}NO_4$ |
| Formula weight | 307.29 |
| Temperature | 296(2) K |
| Wavelength | 0.71073 Å |
| Crystal size | 0.050 × 0.080 × 0.150 mm³ |
| Crystal system | monoclinic |
| Space group | P 1 21/c 1 |
| Unit cell dimensions | a = 7.5352(8) Å    α = 90° |
|  | b = 11.7589(10) Å   β = 95.301(6)° |
|  | c = 15.6709(14) Å   γ = 90° |
| Volume | 1382.6(2) Å³ |
| Z | 4 |
| Density (calculated) | 1.476 mg/cm³ |
| Absorption coefficient | 0.106 mm⁻¹ |
| F(000) | 640 |
| Theta range for data collection | 2.17 to 25.00° |
| Index ranges | −8 <= h <= 8, −13 <= k <= 13, −18 <= l <= 18 |
| Reflections collected | 9965 |
| Independent reflections | 2423 [R(int) = 0.0233] |
| Coverage of independent reflections | 99.8% |
| Absorption correction | multi-scan |
| Max. and min. transmission | 0.9947 and 0.9843 |
| Structure solution technique | direct methods |
| Structure solution program | SHELXS-97 (Sheldrick, 2008) |
| Refinement method | Full-matrix least-squares on $F^2$ |
| Refinement program | SHELXL-97 (Sheldrick, 2008) |
| Function minimized | $\Sigma\, w(F_o^2 - F_c^2)^2$ |
| Data/restraints/parameters | 2423/0/213 |
| Goodness-of-fit on $F^2$ | 1.040 |
| $\Delta/\sigma_{max}$ | 0.001 |
| Final R indices | 1965 data;   $R_1$ = 0.0351, |
|  | I > 2σ(I)     $wR_2$ = 0.0901 |
| R indices (all data) | $R_1$ = 0.0465, |
|  | $wR_2$ = 0.0977 |
| Weighting scheme | $w = 1/[\sigma^2(F_o^2) + (0.0511P)^2 + 0.2796P]$ where $P = (F_o^2 + 2F_c^2)/3$ |
| Largest diff. peak and hole | 0.138 and −0.166 eÅ⁻³ |
| R.M.S. deviation from mean | 0.035 eÅ⁻³ |

(2) Single Crystal Structure of 6-hydroxy-5,8-dimethoxy-7H-azulene [1,2,3-i,j] isoquinolin-7-one Non-hydrogen atomic coordinates and thermal parameters of 6-hydroxy-5,8-dimethoxy-7H-azulene [1,2,3-i,j] isoquinolin-7-one are listed in Table 3, partial bond lengths and bond angles are listed in Tables 4 and 5.

TABLE 3 atomic coordinates and thermal parameters (Å²) of 6-hydroxy-5,8-dimethoxy-7H-azulene [1,2,3-i,j] isoquinolin-7-one

|  | x/a | y/b | z/c | U(eq) |
|---|---|---|---|---|
| O4 | 0.54332(17) | 0.36641(9) | 0.03189(7) | 0.0499(3) |
| O1 | 0.88401(17) | 0.01371(10) | 0.68249(7) | 0.0518(3) |
| O2 | 0.78729(16) | 0.14489(9) | 0.79346(6) | 0.0461(3) |
| O3 | 0.66800(16) | 0.27925(9) | 0.89912(7) | 0.0468(3) |
| N1 | 0.77066(18) | 0.85096(11) | 0.10287(8) | 0.0449(4) |
| C18 | 0.4696(3) | 0.42065(15) | 0.10268(11) | 0.0525(5) |
| C12 | 0.5949(2) | 0.25617(13) | 0.04246(9) | 0.0374(4) |
| C13 | 0.6633(2) | 0.20968(12) | 0.96562(9) | 0.0339(3) |
| C14 | 0.71886(18) | 0.09709(12) | 0.96788(9) | 0.0314(3) |
| C16 | 0.79460(18) | 0.01647(12) | 0.90842(9) | 0.0314(3) |
| C1 | 0.82203(19) | 0.04581(12) | 0.82173(9) | 0.0351(3) |
| C2 | 0.8853(2) | 0.96352(13) | 0.76058(10) | 0.0387(4) |
| C17 | 0.9179(4) | 0.94719(18) | 0.60936(12) | 0.0780(7) |
| C15 | 0.70583(18) | 0.03724(12) | 0.04503(9) | 0.0334(3) |
| C10 | 0.64227(19) | 0.08017(13) | 0.11938(9) | 0.0369(4) |
| C11 | 0.5851(2) | 0.19540(13) | 0.11632(9) | 0.0397(4) |
| C9 | 0.6447(2) | 0.00142(15) | 0.18679(10) | 0.0459(4) |
| C8 | 0.7068(2) | 0.89220(15) | 0.17502(11) | 0.0488(4) |
| C7 | 0.76780(19) | 0.92678(13) | 0.03904(9) | 0.0359(4) |
| C6 | 0.82580(19) | 0.91211(12) | 0.95254(9) | 0.0347(3) |
| C5 | 0.8997(2) | 0.80954(13) | 0.92658(10) | 0.0413(4) |
| C4 | 0.9524(2) | 0.78497(13) | 0.84766(11) | 0.0452(4) |
| C3 | 0.9412(2) | 0.85373(13) | 0.77388(11) | 0.0447(4) |

Figure 9:
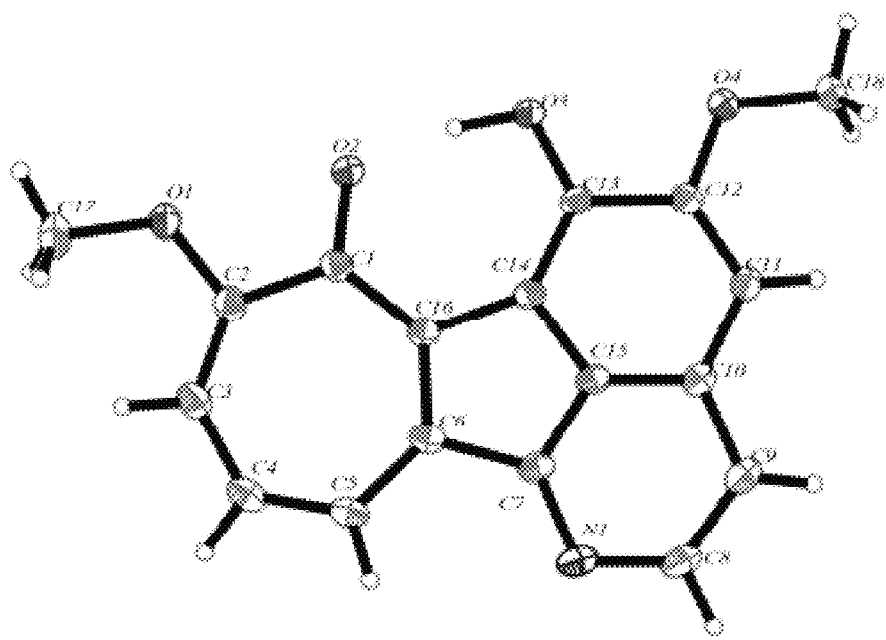
FIG. 9 X-ray single crystal diffraction structure of 6-hydroxy-5,8-dimethoxy-7H-azulene [1,2,3-i,j] isoquinolin-7-one.

Note:
structure number sequence in Table 3 is shown in FIG. 9.

TABLE 4 bond lengths of 6-hydroxy-5,8-dimethoxy-7H-azulene [1,2,3-i,j] isoquinolin-7-one

| chemical bond | bond length Å |
|---|---|
| O4—C12 | 1.3590(18) |
| O1—C2 | 1.3578(18) |
| O2—C1 | 1.2652(18) |
| O3—H6 | 0.99(2) |
| N1—C8 | 1.359(2) |
| C18—H1 | 0.96 |
| C12—C11 | 1.368(2) |
| C13—C14 | 1.388(2) |
| C14—C16 | 1.480(2) |
| C16—C1 | 1.435(2) |
| C2—C3 | 1.368(2) |
| C17—H13 | 0.96 |
| C15—C7 | 1.386(2) |
| C10—C9 | 1.404(2) |
| C11—H7 | 0.93 |
| C9—H12 | 0.93 |
| C7—C6 | 1.472(2) |
| C5—C4 | 1.364(2) |
| C4—C3 | 1.407(2) |
| C3—H8 | 0.93 |
| O4—C18 | 1.4354(18) |
| O1—C17 | 1.430(2) |
| O3—C13 | 1.3279(17) |
| N1—C7 | 1.3387(19) |
| C18—H5 | 0.96 |
| C18—H4 | 0.96 |
| C12—C13 | 1.459(2) |
| C14—C15 | 1.4100(19) |
| C16—C6 | 1.417(2) |
| C1—C2 | 1.417(2) |

TABLE 4-continued bond lengths of 6-hydroxy-5,8-dimethoxy-7H-azulene
[1,2,3-i,j] isoquinolin-7-one

| chemical bond | bond length Å |
|---|---|
| C17—H3 | 0.96 |
| C17—H2 | 0.96 |
| C15—C10 | 1.395(2) |
| C10—C11 | 1.421(2) |
| C9—C8 | 1.385(2) |
| C8—H11 | 0.93 |
| C6—C5 | 1.405(2) |
| C5—H10 | 0.93 |
| C4—H9 | 0.93 |

Note:
structure number sequence in Table 3 is shown in FIG. 9.

TABLE 5 bond angles of 6-hydroxy-5,8-dimethoxy-7Z7-azulene
[1,2,3-i,j] isoquinolin-7-one

| chemical bond | bond angle ° |
|---|---|
| C12—O4—C18 | 117.15(12) |
| C13—O3—H6 | 106.5(11) |
| O4—C18—H5 | 109.5 |
| H5—C18—H1 | 109.5 |
| H5—C18—H4 | 109.5 |
| O4—C12—C11 | 124.35(14) |
| C11—C12—C13 | 123.59(14) |
| O3—C13—C12 | 116.99(13) |
| C13—C14—C15 | 116.95(13) |
| C15—C14—C16 | 106.35(12) |
| C6—C16—C14 | 107.67(12) |
| O2—C1—C16 | 120.64(13) |
| C16—C1—C2 | 122.82(13) |
| O1—C2—C1 | 108.99(13) |
| O1—C17—H3 | 109.5 |
| H3—C17—H13 | 109.5 |
| H3—C17—H2 | 109.5 |
| C7—C15—C10 | 122.65(13) |
| C10—C15—C14 | 126.31(14) |
| C15—C10—C11 | 116.32(13) |
| C12—C11—C10 | 119.11(14) |
| C10—C11—H7 | 120.4 |
| C8—C9—H12 | 120.2 |
| N1—C8—C9 | 126.28(14) |
| C9—C8—H11 | 116.9 |
| N1—C7—C6 | 128.63(14) |
| C5—C6—C16 | 130.88(14) |
| C16—C6—C7 | 107.32(12) |
| C4—C5—H10 | 116.5 |
| C5—C4—C3 | 128.53(15) |
| C3—C4—H9 | 115.7 |
| C2—C3—H8 | 114.3 |
| C2—O1—C17 | 119.85(14) |
| C7—N1—C8 | 113.68(14) |
| O4—C18—H1 | 109.5 |
| O4—C18—H4 | 109.5 |
| H1—C18—H4 | 109.5 |
| O4—C12—C13 | 112.06(12) |
| O3—C13—C14 | 125.30(13) |
| C14—C13—C12 | 117.71(12) |
| C13—C14—C16 | 136.69(13) |
| C6—C16—C1 | 129.64(13) |
| C1—C16—C14 | 122.66(13) |
| O2—C1—C2 | 116.51(13) |
| O1—C2—C3 | 121.59(14) |
| C3—C2—C1 | 129.41(14) |
| O1—C17—H13 | 109.5 |
| O1—C17—H2 | 109.5 |
| H13—C17—H2 | 109.5 |
| C7—C15—C14 | 111.04(13) |
| C15—C10—C9 | 114.10(15) |
| C9—C10—C11 | 129.58(15) |
| C12—C11—H7 | 120.4 |

TABLE 5-continued bond angles of 6-hydroxy-5,8-dimethoxy-7Z7-azulene
[1,2,3-i,j] isoquinolin-7-one

| chemical bond | bond angle ° |
|---|---|
| C8—C9—C10 | 119.52(15) |
| C10—C9—H12 | 120.2 |
| N1—C8—H11 | 116.9 |
| N1—C7—C15 | 123.76(14) |
| C15—C7—C6 | 107.61(12) |
| C5—C6—C7 | 121.79(14) |
| C4—C5—C6 | 126.93(15) |
| C6—C5—H10 | 116.5 |
| C5—C4—H9 | 115.7 |
| C2—C3—C4 | 131.43(15) |
| C4—C3—H8 | 114.3 |

Note:
structure number sequence in Table 3 is shown in FIG. 9.

Figure 10:
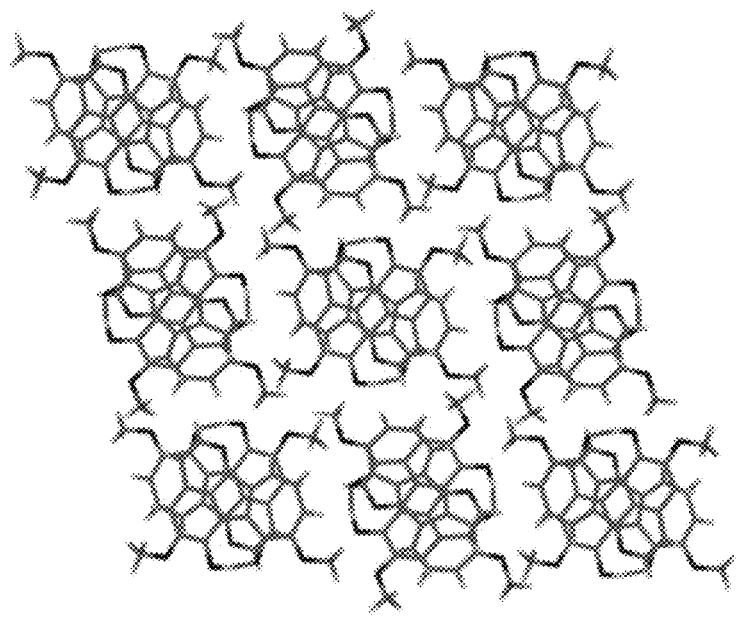
FIG. 10 unit cell stacking diagram of 6-hydroxy-5,8-dimethoxy-7H-azulene [1,2,3-i,j] isoquinolin-7-one.

FIG. 9 illustrates a single crystal diffraction structure of 6-hydroxy-5,8-dimethoxy-7H-azulene [1,2,3-i,j] isoquinolin-7-one. FIG. 10 is a cell stacking diagram thereof.

The single crystal of 6-hydroxy-5,8-dimethoxy-7H-azulene [1,2,3-i,j] isoquinolin-7-one belongs to a monoclinic system and the space group is P 1 21/c 1. Unit cell parameters are: a=7.5352(8) Å, b=11.7589(10) Å, c=15.6709(14) Å, α=90°, β=95.301(6)°, γ=90°; Z=4, V=1382.6(2) Å3, $D_c$=1.476 mg/cm$^3$, F(000)=640, μ=0.09 mm$^{-1}$, 1965 observable points [I>2σ(I)], observable point refinement final deviation factor R1=0.0351, wR2=0.0901.

In the crystal structure of 6-hydroxy-5,8-dimethoxy-7H-azulene [1,2,3-i,j] isoquinolin-7-one, the intermolecular structure is maintained stable by π-π interaction.

Embodiment 5

Protective Effect of
6-hydroxy-5,8-dimethoxy-7H-azulene [1,2,3-i,j]
isoquinolin-7-one on Damaged Nerve Cells Sample: 6-hydroxy-5,8-dimethoxy-7H-azulene [1,2,3-i,j] isoquinolin-7-one.

Cell line: PC12 cells (rat adrenal medullary pheochromocytoma clone), highly differentiated, purchased from Changsha Yingrun Biotechnology Co., Ltd.

Reagents: DMEM high sugar medium, D-Hanks (Solarbio, no calcium and magnesium, no phenol red), 100× penicillin-streptomycin solution (Beyotime), fetal bovine serum (FBS) (gibco), trypsin (Beijing Suo Labao), tetramethylazo salt method (Sigma, USA), β amyloid protein (Aβ$_{25-35}$) (Sigma, USA), sterile 96-well plate (NEST).

Instruments: HFsafe-1500 ultra-clean workbench, HF151UV CO$_2$ incubator (Shanghai Lishen Scientific Instrument Co., Ltd.); XSP-15C inverted microscope (Shanghai Changfang Optical Instrument Co., Ltd.); Multiskan MK3 microplate reader (USA Thermo); ultrapure water preparation instrument (Milli-Q, USA).

Cell culture: culturing PC12 cells cultured in TC-treated flasks, wherein a DEME high-sugar medium (pH 7.2) was adopted, containing 10% fetal bovine serum, 100 U·mL$^{-1}$ penicillin, 100 g·mL$^{-1}$ streptomycin; incubating at 37° C. in 5% CO$_2$ cell culture incubator; when cell adherence is up to 90%, digesting with 0.25% trypsin, then add perfusate and pipetting to a single cell suspension; passing or inoculating to an appropriate culture plate, and keeping incubating for 48 h as experimental cells.

Determination of viability of PC12 cells by Aβ$_{25-35}$ with different concentrations: the cultured PC12 cells were seeded at $1\times10^4$ cells/well in a 96-well plate, and the cells were grown to a logarithmic growth phase and replaced with serum-free medium for subsequent use. The experiment was divided into 8 groups, 4 wells in each group. The blank control group: 200 μL of serum-free medium to each well. The $A\beta_{25-35}$ model group: each group was added with serum-free medium for preparing 200 μL $A\beta_{25-35}$ solution with final concentration of 5, 10, 20, 30, 40, 50 and 60 μmol/L; the cells were cultured in an incubator containing 5% $CO_2$ at 37° C. for 24 h, and the cell viability was measured with MTT by: adding 10 μL of an MTT solution (prepared by PBS at a concentration of 5 mg·mL$^{-1}$) into the wells; after incubating for 4 h in the cell culture incubator, taking out and quickly flipping the 96-well plate; vertically flapping to remove the solution in the wells, so avoid cross-interference; adding 100 μL of dimethyl sulfoxide (DMSO), measuring optical density (OD) of each well under 490 nm with enzyme-linked immunosorbent assay, and calculating cell viability, so as to determine concentration required for $A\beta_{25-35}$ induced PC12 cells oxidative stress response model.

Cell viability/%=(drug group OD−blank control group OD)/(control group−blank group OD)× 100%

Protective effect of 6-hydroxy-5,8-dimethoxy-7H-azulene [1,2,3-i,j] isoquinolin-7-one on PC12 cells damaged by $A\beta_{25-35}$: cell seeding in the 96-well plate was the same as above, and the experiment was divided into 5 groups, 4 holes in each group. Blank control group: 200 μL of serum-free medium to each well; $A\beta_{25-35}$ model group: each group was added with serum-free medium for preparing 200 μL $A\beta_{25-35}$ solution with final concentration of 30 μmol/L; drug treatment group: each group was added with serum-free medium for preparing drugs with final concentration of 0.5, 1.0 and 5.0 μg·mL$^{-1}$, and then $A\beta_{25-35}$ was added to a final concentration of 30 μmol·L$^{-1}$; wherein final volume of each well was 200 μL; culture and determination methods are the same as above.

Statistical methods: data were represented with $\bar{x}=s$, t test was used for comparison between groups, $P<0.05$ was considered as significant difference, and $P<0.01$ was extremely significant difference, which was statistically significant.

Experimental Results:

(1) Determination of viability of PC12 cells by $A\beta_{25-35}$ with different concentrations: after $A\beta_{25-35}$ with different concentrations and PC12 cells were incubated together for 24 h, the cell viability decreased significantly, wherein in the range of 10-40 μmol·L$^{-1}$, $A\beta_{25-35}$ had a significant dose-related association with PC12 cell damage. 5 μmol·L$^{-1}$ $A\beta_{25-35}$ had very little cell damage, only a small number of cells became round. As the concentration increased, the cells aggregated and fell off, which are diffused, and the cell viability also decreased linearly. When the concentration was as high as 40-60 μmol·L$^{-1}$, the degree of damage was similar, and the change was not significant. In this experiment, $A\beta_{25-35}$ with a concentration of 30 μmol·L$^{-1}$ was selected as the damage concentration of the damaged nerve cell model.

(2) Protective Effect of 6-hydroxy-5,8-dimethoxy-7H-azulene [1,2,3-i,j] isoquinolin-7-one on PC12 cells damaged by $A\beta_{25-35}$:

TABLE 6 protective effect of 6-hydroxy-5,8-dimethoxy-7H-azulene [1,2,3-i,j] isoquinolin-7-one on PC12 cells damaged by $A\beta_{25-35}$ ($\bar{x} \pm s$, n = 4)

| sample | concentration (ug · mL$^{-1}$) | cell viability (%) |
|---|---|---|
| blank control | | 100.00 ± 0.97 |
| model | | 51.90 ± 1.88* |
| 6-hydroxy-5,8-dimethoxy-7H-azulene [1,2,3-i,j] isoquinolin-7-one | 0.5 | 85.80 ± 1.60** |
| | 1.0 | 102.80 ± 1.80** |
| | 5.0 | 77.40 ± 3.80** |

*P < 0.01 compared with blank control group;
**P < 0.01 compared with model group From the analysis of Table 6, it was found that compared with blank control group, the cell viability was significantly decreased after adding 30 μmol·L$^{-1}$ $A\beta_{25-35}$ injury factor (P<0.01). Compared to model group, 6-hydroxy-5,8-dimethoxy-7H-azulene [1,2,3-i,j] isoquinolin-7-one with three different concentrations all significantly increased cell viability (P<0.01), wherein viability of PC12 damaged cells was >95% at a concentration of 1.0 μg·mL$^{-1}$. The compound of 7H-azulene [1,2,3-i,j] isoquinolin-7-one can be used for preparing a drug for diseases caused by damaged nerve cells, especially for the treatment of senile dementia, stroke and epilepsy.

The above description is only the preferred embodiment of the present invention, and is not intended to limit the present invention, and various modifications and changes can be made to the present invention. Any modifications, equivalent substitutions, improvements, etc. made within the spirit and scope of the present invention are intended to be included within the scope of the present invention.

What is claimed is:

1. A single crystal of a compound as shown in a formula (II), wherein the single crystal has following single crystal structure parameters:

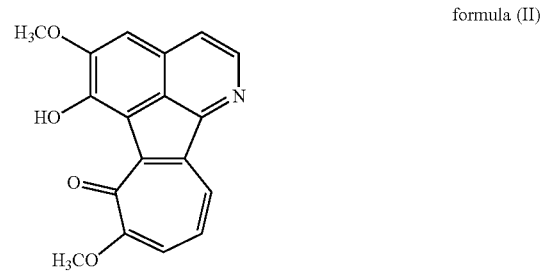 [SMILES: COc1cc2ccnc3c2c(c1O)-c1c-3cccc(OC)c1=O]

formula (II)

| | |
|---|---|
| crystal system | monoclinic system |
| space group | P121/c1 |
| cell parameters | a = 7.5352(8) Å, α = 90°, |
| | b = 11.7589(10) Å, β = 95.301(6)°, |
| | c = 15.6709(14) Å, γ = 90°, |
| volume | 1382.6(2) Å$^3$ |
| number of molecules per unit cell Z: | 4 |

2. A method for preparing a single crystal as recited in claim 1, comprising steps of: dissolving a crude compound of a formula (II) in a solvent and standing, sealing when crystals are precipitated, keeping standing to obtain the single crystal.

3. A method for preparing a compound as shown in a formula (II), comprising steps of: washing *Acorus calamus* L. for removing impurities, pulverizing into coarse powder, extracting with an alcohol solvent, and concentrating an extract under a reduced pressure until the extract is viscous, so as to obtain an alcohol extract;

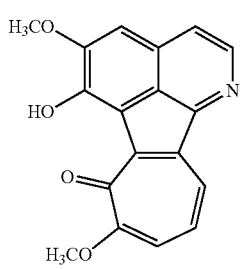

formula (II)

suspending the alcohol extract in water, extracting with different polar solvents in sequence, concentrating a solvent extract under a reduced pressure; and separating residue by column chromatography to obtain the compound as shown in the formula (II).

4. The method, as recited in claim 3, wherein the alcohol solvent is a $C_{1-4}$ alcohol solvent.

5. The method, as recited in claim 2, wherein the solvent is a methanol, ethanol, chloroform or a chloroform-methanol mixed solution.

* * * * *